United States Patent
Humphrey

(10) Patent No.: US 8,537,373 B2
(45) Date of Patent: Sep. 17, 2013

(54) POSITION DETECTION

(75) Inventor: Malcolm Humphrey, West Sussex (GB)

(73) Assignee: Elekta AB (Publ), Stockholm (SE)

( * ) Notice: Subject to any disclaimer, the term of this patent is extended or adjusted under 35 U.S.C. 154(b) by 0 days.

(21) Appl. No.: 13/593,203

(22) Filed: Aug. 23, 2012

(65) Prior Publication Data

US 2013/0003080 A1    Jan. 3, 2013

Related U.S. Application Data

(63) Continuation-in-part of application No. PCT/EP2010/001265, filed on Mar. 2, 2010, and a continuation-in-part of application No. PCT/EP2010/001266, filed on Mar. 2, 2010.

(51) Int. Cl.
 *G01B 11/14* (2006.01)
 *G21K 1/04* (2006.01)

(52) U.S. Cl.
 USPC ............ 356/614; 378/152; 378/65; 378/69; 250/234

(58) Field of Classification Search
 USPC .......... 356/614–623; 378/65, 206, 145–153; 250/234, 505.01
 See application file for complete search history.

(56) References Cited

U.S. PATENT DOCUMENTS

| | | | |
|---|---|---|---|
| 4,502,147 A | 2/1985 | Michaels | |
| 4,882,741 A * | 11/1989 | Brown | 378/152 |
| 6,104,778 A | 8/2000 | Murad | |
| 7,020,245 B2 * | 3/2006 | Noguchi | 378/150 |
| 7,040,807 B2 | 5/2006 | Scheuering | |
| 7,095,823 B2 * | 8/2006 | Topolnjak et al. | 378/152 |
| 7,729,744 B2 * | 6/2010 | Falco et al. | 600/427 |
| 2002/0052710 A1 | 5/2002 | Hwang | |
| 2004/0240621 A1 | 12/2004 | Noguchi | |
| 2006/0072849 A1 * | 4/2006 | Marc | 382/291 |
| 2008/0205599 A1 | 8/2008 | Hashimoto | |
| 2008/0298553 A1 | 12/2008 | Takahashi | |
| 2009/0080619 A1 * | 3/2009 | Hasegawa et al. | 378/151 |

FOREIGN PATENT DOCUMENTS

| | | |
|---|---|---|
| EP | 0314231 A2 | 5/1989 |
| EP | 1961446 A1 | 8/2008 |
| EP | 2085117 A1 | 8/2009 |
| JP | 2009095647 A | 5/2009 |

OTHER PUBLICATIONS

International Search Report for PCT/EP2010/001265, Oct. 29, 2010.
Written Opinion, PCT/EP2010/001265, Oct. 29, 2010.
International Search Report for PCT/EP2010/001266, Dec. 10, 2010.
Written Opinion, PCT/EP2010/001266, Dec. 10, 2010.

* cited by examiner

*Primary Examiner* — Hoa Pham
(74) *Attorney, Agent, or Firm* — Westman, Champlin & Kelly, P.A.; Z. Peter Sawicki

(57) ABSTRACT

Apparatus for location-detection of an object within a region comprising a reflective element mountable on the object, a scanning light source adapted to issue a beam of light in a scanning pattern illuminating a point that moves over the region, a detector for light reflected from the reflective element and a control unit adapted to report the position of an object based on the point in the scanning pattern at which the detector detects light returned from the reflective element relative to at least one point in the scanning pattern at which the detector detects light returned from a reflective object.

10 Claims, 3 Drawing Sheets

POSITION DETECTION

CROSS REFERENCE TO RELATED APPLICATIONS

This application is a continuation-in-part application of International Application No. PCT/EP2010/001265, filed Mar. 2, 2010 and published as WO 2011/107111 A1 on Sep. 9, 2011, the content of which is hereby incorporated by reference in its entirety and a continuation-in-part of Application No. PCT/EP2010/001266, filed Mar. 2, 2010 and published as WO/2011/107112 A1 on Sep. 9, 2011, the content of which is hereby incorporated by reference in its entirety.

FIELD OF THE INVENTION

The present invention relates to an improved form of position detection. It is especially (but by no means solely), suitable for the detection of leaf positions in a Multi-Leaf Collimator ("MLC") for use in radiotherapeutic apparatus.

BACKGROUND ART

There are a wide range of contexts in which it is necessary to determine the position of a remote object. One particularly difficult context is in tracking the positions of individual leaves of a multi leaf collimator (MLC) in a linear accelerator (Linac). An MLC is used to shape the beam of X-ray (or other) radiation produced by a linac, in order to treat a patient. For the control system to deliver a correctly shaped dose, the position of each leaf must be accurately determined. Current methods that are employed use a combination of a standard CCTV camera and reflectors positioned on each leaf. A source of light illuminates the area in which the reflectors lie, and the CCTV camera receives an image that includes the reflections. The position of each leaf can then be determined from the position of each reflection within the CCTV camera image.

The main problem with such systems is that the accuracy and resolution are limited by the number of pixels within the camera. This cannot be easily increased. In addition, most electronics (including CCTV cameras) are susceptible to radiation, and will eventually break down if exposed to significant levels. Radiation hardened cameras can be designed, but these are expensive and are usually bespoke, so are not readily available.

Most CCTV cameras also have a limited frame rate of (typically) 30 frames per second at most. Where fast movements are required of the MLC leaves, this frame rate may not be adequate to keep up.

Video processing software is also required, which is computationally demanding and therefore increases system complexity and cost.

The CCTV camera is bulky, and needs to be fitted into an area where space is at a premium.

Electromagnetic noise generated from within the Linac can interfere with the image quality and may interfere with the image processing software, causing a loss of leaf positions.

Other contexts exist in which similar problems are encountered, however.

Finally, CCTV cameras are responsive to a broad range of optical wavelengths, making them susceptible to sources of interference such as room lasers, fluorescent lights, and the like.

SUMMARY OF THE INVENTION

The present invention therefore provides apparatus for location-detection of a plurality of objects within a region, comprising a reflective element mountable on each object of the plurality, and a plurality of reflective objects mounted at extremities of the region, a scanning light source adapted to issue a beam of light in a scanning pattern illuminating a point that moves over the region, and a detector for light reflected from the reflective elements or the reflective objects, together with a control unit adapted to report the position of an object based on the point in the scanning pattern at which the detector detects light returned from the reflective element relative to at least one point in the scanning pattern at which the detector detects light returned from a reflective object. The scan can then be repeated, as necessary.

It further provides a multi-leaf collimator comprising an array of laterally spaced elongate leaves each having a longitudinal edge on which is mounted a reflective element, a scanning light source adapted to issue a beam of light in a scanning pattern, illuminating a point that moves over the longitudinal edges of a plurality of leaves of the array, and a detector for light reflected from the reflective elements.

The scanning light source can comprise a source of light that illuminates a mirror, the mirror being controllably adjustable so as to direct a reflected beam of light in a scan pattern. The mirror is preferably part of a micro-electromechanical ("MEMS") device, so as to allow swift and accurate control of the mirror position.

The reflective objects are preferably fixed, so that the return signal that they produce when illuminated can occur at a fixed point in the scan cycle, making it straightforward to identify a return signal corresponding to a reflective element.

At least one other mirror is preferably located (or locatable) in the radiation beam path, to permit the scanning light source to be located out of the beam path thereby protecting it from incident radiation.

The scanning pattern can be a raster pattern, or a serpentine pattern, or another form of scanning pattern. It preferably illuminates a point that moves along the longitudinal edges of a plurality of leaves of the array in succession. Other scanning patterns are possible, however.

The scanning light source can comprise a laser.

The reflective element is preferably retro-reflective.

The invention also relates to a radiotherapeutic apparatus comprising such a multi-leaf collimator.

Tracking objects using MEMs mirrors and laser light is known, for example from U.S. Pat. No. 7,498,811 or from "Fast and high-precision 3D tracking and position measurement with MEMs micromirrors" Milanovic, V. & Wing, Kin Lo, *IEEE/LEOS International Conference on Optical MEMs and Nanophotonics,* 2008 (pp 72-73). However, it does not appear to have been applied to the detection of leaf positions in an MLC array. The Milanovic system also needs to interrogate the MEMS driver in order to ascertain the position of the mirror at the instant when the signal is detected or reflected. By placing reflective objects at known locations within the region and/or reflective elements on the moving object, the complexity and the cost of the system is reduced, and the accuracy of the system is improved, and multiple object positions (such as MLC leaves) can be tracked within the laser scanning field of view. In addition, placing so-called "boundary markers" allows the system to determine the object position relative to the boundary markers using simple algorithms based on the signal time measurements, and avoids the need to interrogate the MEMS driver. The reflective objects need not be at the actual boundaries of the region, although that is likely to be particularly straightforward to implement.

The invention also provides a corresponding method.

BRIEF DESCRIPTION OF THE DRAWINGS

An embodiment of the present invention will now be described by way of example, with reference to the accompanying figures in which.

DETAILED DESCRIPTION OF THE EMBODIMENTS

The following embodiment of the present invention is a position-detection system for the leaves of a multi-leaf collimator. This faces significant difficulties as set out above, which are alleviated by the present invention. However, the invention is also applicable in other contexts.

Figure 1:
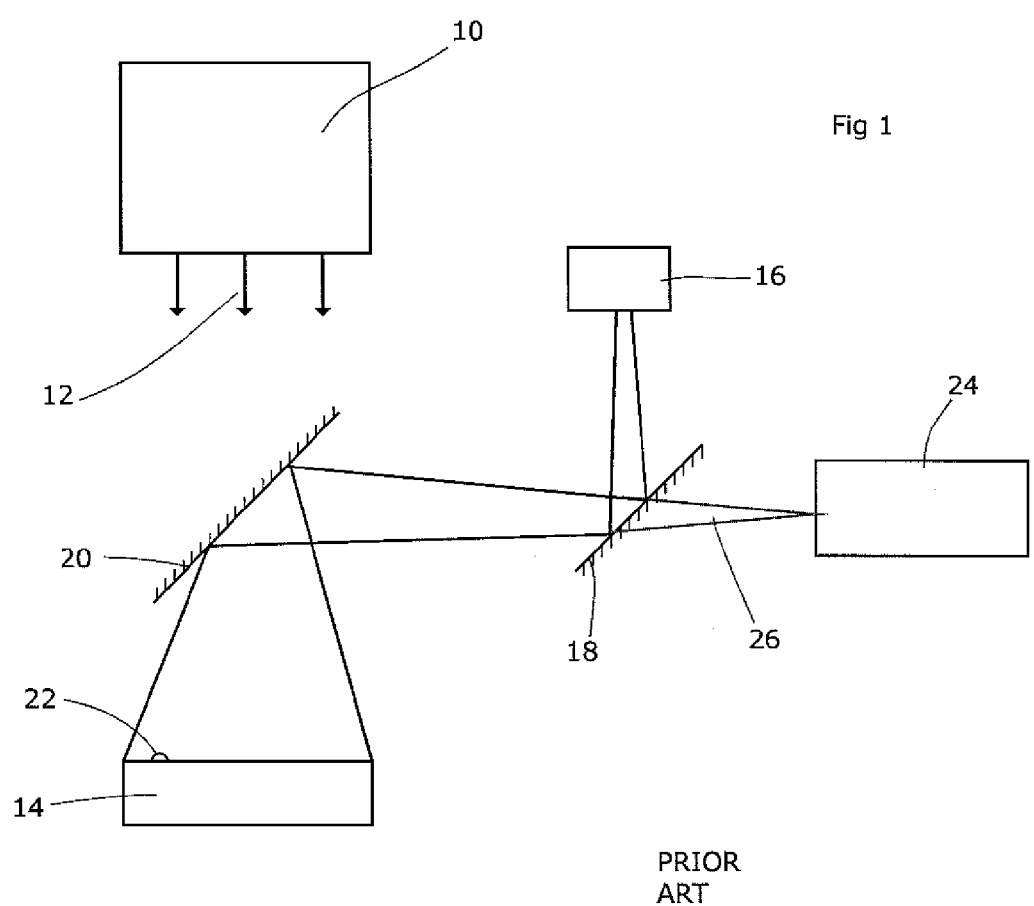
FIG. 1 shows a known solution in the context of a radiotherapy system, based on a video camera.

FIG. 1 shows a known position tracking system for an array of MLC leaves. A radiation source 10 emits a beam of radiation 12 towards a treatment volume, illustrated (by convention) as being in a downward direction. In practice, the source is usually rotated around the treatment volume so as to irradiate the region of interest from a range of different angles, thereby reducing the irradiation of surrounding tissue.

The shape of the radiation beam 12 is collimated by an MLC comprising an array of individual leaves 14. These are deep in the beam direction, elongate, and narrow in width. They are arranged side-by-side, and are individually moveable back and forth, into and out of the beam. Thus, a large number of such leaves can shape the beam as required. Typical MLCs include 40, 80 or 160 leaves depending on the desired resolution.

The leaves are driven by an electric motor. In order to place the motor out of the beam and protect it from radiation damage, and in order to fit the required number of motors within the available space, the motors are usually spaced some distance from the leaf that they control and the necessary torque is transmitted from the motor to the leaf by a mechanical arrangement. The correct movement of the leaf is therefore subject to correct programming of the motor control unit, correct operation of the motor, and correct operation of whatever mechanical link is employed. It is therefore necessary to verify that the leaf is in fact in the correct position, to allow for failsafe operation of the apparatus.

As shown in FIG. 1, this is achieved by providing a light source 16 to one side of the radiation source 10, which illuminates the MLC leaves via a pair of periscopically arranged mylar mirrors 18, 20. A reflector 22 is attached to a known location on an upper (in the orientation shown in FIG. 1) surface of the leaf 14, and reflects light back via the mirrors to a video camera co-located with the light source 16. The camera therefore records an image from which the position of each leaf is obtainable. This can be compared to the intended position of each leaf, and the treatment halted if an error greater than a certain magnitude is detected.

FIG. 1 also shows the field lamp 24. This emits a light beam 26 which is incident on the rear of the first mylar mirror 18 through which at least part of the beam is transmitted. That then falls on the second mirror 20 and is reflected toward the treatment volume. Both the source/camera 16 and the field lamp 24 are positioned relative to the radiation source and the mirrors 18, 20 so that they are in a location that is optically identical to that of the radiation source 10. Thus, the camera receives a beam's-eye view of the leaves 14, and the field lamp illuminates the treatment volume in the same manner as the radiation, allowing it to be used for pre-treatment alignment of the patient.

This form of camera is however undesirable for the reasons noted above.

Figure 2:
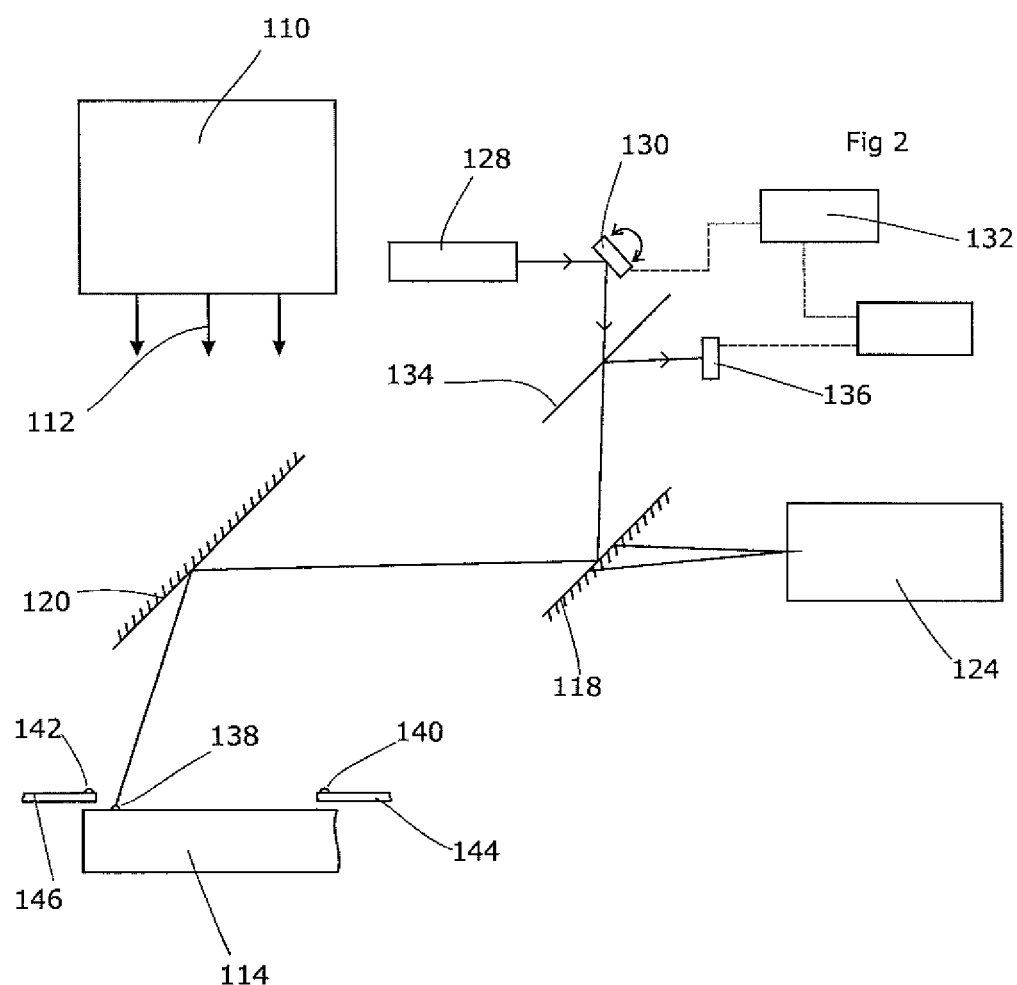
FIG. 2 shows an arrangement according to the present invention, implemented by way of example on a radiotherapy system.

FIG. 2 shows an embodiment of the present invention. As before, a radiation source 110 emits a beam of radiation 112 towards a treatment volume, and the shape of the radiation beam 112 is collimated by an MLC comprising an array of individual leaves 114. A laser light source 128 is also provided, directed towards a 2D MEMs (Micro-Electra-Mechanical Systems) scanning mirror 130. This is controlled by a driver 132, which is programmed to cause the mirror 130 to oscillate so as to scan the laser light beam across each leaf 114 of the MLC, as described later. To direct the laser light to the leaves 114, mylar mirrors 118, 120 are provided as before.

A beam splitter 134 is placed in the path of the laser light, between the oscillating mirror 130 and the first mylar mirror. This directs at least some of the laser light returned from the leaves 114 to a photo sensor 136 capable of detecting the laser light.

On top of each leaf 114 is a retro-reflector 138 which reflects the laser light back in the direction from which it came, back towards the photo sensor 136. The time lapse between the laser light being reflected from the reference reflector and from the retro-reflector 138 is then used to determine the location of the retro-reflector 138, and thus the location of the leaf 114. The mirror then scans the laser beam along the length of the next leaf, repeating the process. In practice, the relevant position of the mirror is that which existed a few nanoseconds before receipt of the reflected light, to allow for travel time of up to about a metre in total. However, this small delay is unlikely to make a difference in practice.

A means for calibrating the motion of the MEMs within each scan cycle is also included. Additional reference reflectors 140, 142 are affixed just beyond the ends of each leaf 114 at the edges of the scan pattern, such as on the supports 144, 146 that surround the leaves 114. In this way, the position of the sinusoidal or other scanning maxima/minima can be measured during each leaf-pair traversal. This can, in turn, be used to calibrate for amplitude and frequency jitter during each scan cycle.

Figure 3:
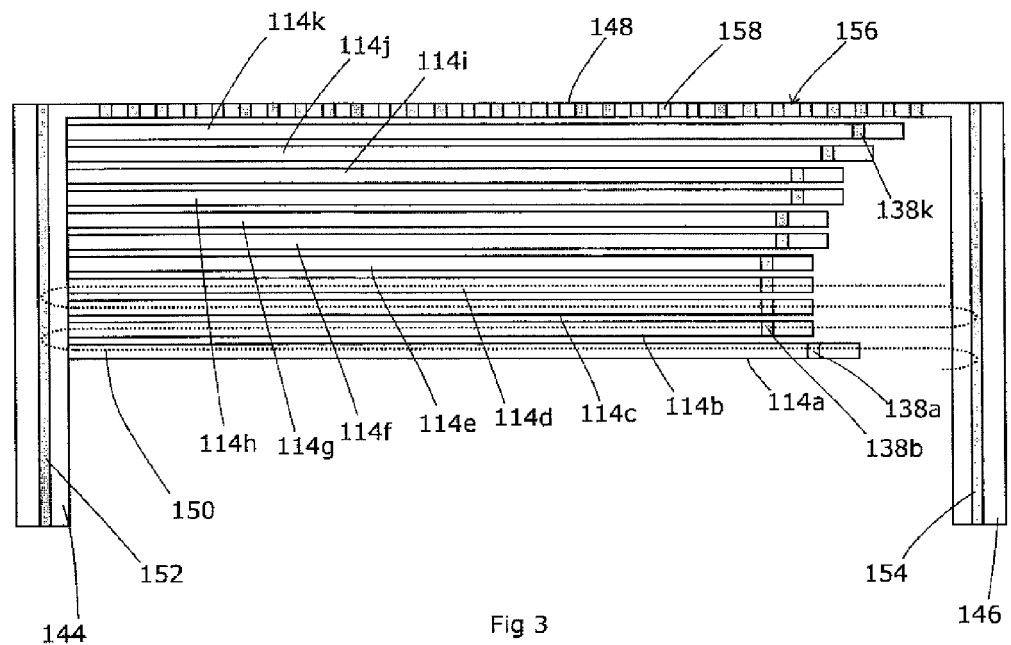
FIG. 3 shows the scanning pattern of FIG. 2.

FIG. 3 shows a suitable scan pattern. Viewed from along the radiation beam axis, the array of leaves 114a-114k sit alongside each other and are at varying positions. They are supported in a frame made up of the supports 144, 146 at either end of travel of the leaves 114 and a side member 148. Further leaves (in addition to those depicted in FIG. 3) sit alongside the illustrated leaves but are omitted for clarity; other elements of the frame are likewise omitted.

Each leaf 114a-114k has a corresponding reflector 138a-138k located at a known position along the leaf. FIG. 3 illustrates a convenient location, in which the reflector is proximate to, but not at, the end of the leaf. Such a location reduces the risk of damage to the reflector during handling.

The oscillating mirror 130 scans the laser light along the serpentine path illustrated by dotted line 150. This takes the light beam along the length of each leaf 114 and will thus prompt a brief return signal as the light passes the respective reflector 138. The path has a maxima/minima that overlaps the supports 144, 146 at either end of travel of the leaves 114, at which points a continuous transverse reflector strip 152, 154 is provided. Thus, there is also a brief return signal at either end of the oscillation. This allows the oscillations to be calibrated, as the time delay between these signals should be constant and predictable, and also provides a frame around the return from the reflector 138 allowing it to be interpreted according to normal principles of pulse position modulation.

Alternatively, a raster pattern can be adopted.

The system also includes an in-built calibration for each scan cycle, to take into account any effects arising from possible non-linearities due to jitter and the sinusoidal nature of the scanning mirror's motion in the fast scanning axis (along the length of the MLC leaves). These effects are calibrated for by the use of one or more fixed calibration strips 156 upon which are mounted a series of reference reflectors 158 in a known pattern on the calibration strip. In this way, a comparison can be made with the theoretical sinusoidal motion of the MEMs mirror 130, and any deviations can be calibrated for. This also eliminates any drift that may arise from changes in temperature or wear in the scanning mirror mechanism over time. As illustrated in FIG. 3, the calibration strip is placed on the side member 148, but could be located elsewhere within the field of view of the detector 136. More than one such calibration strip could be provided.

Figure 4:
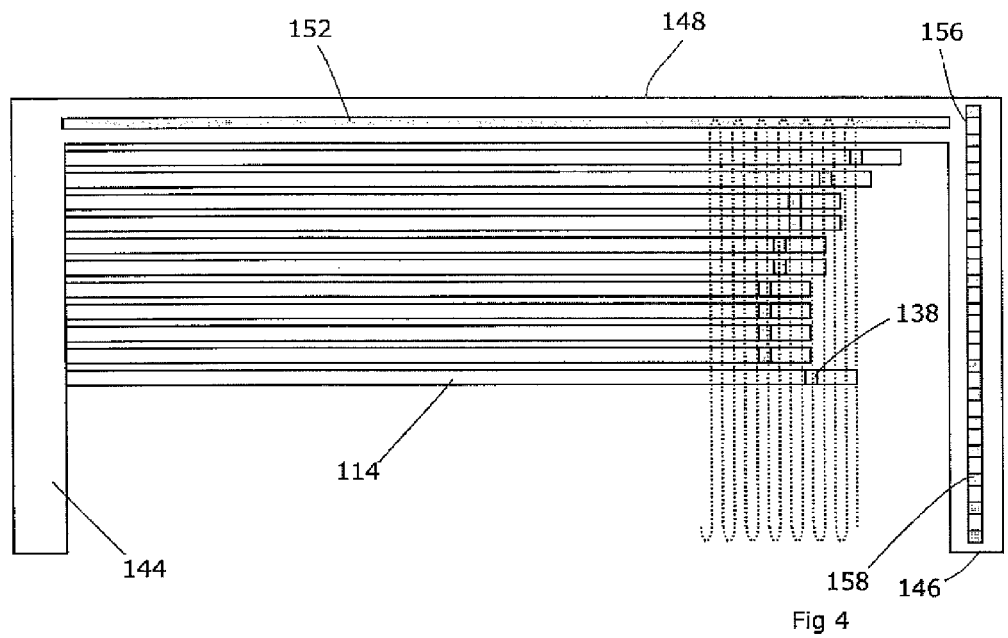
FIG. 4 shows an alternative scan pattern.

FIG. 4 illustrates an alternative scan pattern, also serpentine but transverse to the leaves 114 instead of along the leaves 114. Such a pattern would essentially scan through all the possible leaf positions and report which leaf was in that position, rather than scanning along each leaf and reporting the position of that leaf.

The following advantages can be gained from such a system;

Low cost: none of the active components need to be radiation hard as they can be located away from the direct beam, and are sufficiently small that they can be easily shielded. The mirror device is based upon standard silicon processes and is geared towards mass production. Such a system could easily be 10% of the cost of current camera based systems.

High reliability: The scanning mirror devices are fabricated on silicon using standard processes. There is little or no friction to cause wear, therefore the expected lifetime of the scanning mirror is likely to be in excess of the lifetime of the Linac. The remaining components have no moving parts and can expect to have similar lifetimes. Additionally, the system could be made in such a way that it would not be susceptible to radiation, meaning that (potentially) the components may never need replacement.

Higher accuracy. The accuracy of the system is limited only by the jitter of the controlling electronics, which can be as low as 0.02%. This offers greater potential accuracy when compared with traditional camera based systems. The resolution of the system can easily exceed that of the current camera based system.

Higher scan rate. The achievable scan rate can easily exceed the 30 Hz currently available via a camera based system, allowing faster leaf movements to be tracked safely with improved control.

Lower processing requirements. The algorithm used to determine leaf position is a simple one based on interpolation between the calibration points and the known scan pattern (such as sinusoidal), thus eliminating the need for complex image processing and fast processors to cope with the video data (most of which is discarded).

Smaller size. The scanning mirror device itself is very small (typically 10 mm$^2$). The laser source and the photo sensor are also similarly small in size, thus reducing space requirements for the system.

Reduced interference. The system could be made such that it only responds to one wavelength of light. Filtering this wavelength from entering or leaving the head would be a simple matter, requiring only the necessary optical filters. Additionally, due to the nature of the signals generated (effectively pulse position modulation), the system's susceptibility to electromagnetic interference could be reduced. By using coded pulses of laser light, false pulses from electromagnetic or optical sources could be effectively eliminated.

Redundancy. Due to the small size and low cost of the proposed system, an identical backup system could easily be employed to detect failures.

As mentioned above, the specific embodiment described herein relates to detecting the positions of individual leaves in a multi-leaf collimator, but the invention is not limited to this context and could be applied in other situations. For example, the invention could be used to measure the shape or position of something by having a bank of leaves in contact with a surface of the item concerned. The leaves will then adopt the shape of the surface, which can then be measured. The surface may be mobile, in which case the moving surface will translate into corresponding motion of the leaves which can be measured by the system.

Alternatively, a reflective strip can be affixed directly to a moving object or region, with a stationary reflective strip placed suitably nearby, so that the scanner can scan across both the moving and the stationary markers to determine the distance between them. This could find application in the field of respiration monitors, or in tools for the accurate placement of components in circuit boards, for example.

It will of course be understood that many variations may be made to the above-described embodiment without departing from the scope of the present invention.

What is claimed is:

1. A multi-leaf collimator comprising;
an array of laterally spaced elongate leaves each having a longitudinal edge on which is mounted a reflective element;
a scanning light source adapted to issue a beam of light in a scanning pattern, so as to illuminate a point that moves over the longitudinal edges of a plurality of leaves of the array; and
a detector for light reflected from the reflective elements.

2. The multi-leaf collimator according to claim 1 in which the scanning light source comprises a source of light that illuminates a mirror, the mirror being controllably adjustable so as to direct a reflected beam of light in a scan pattern.

3. The multi-leaf collimator according to claim 2 in which the mirror is part of a micro-electromechanical device.

4. The multi-leaf collimator according to claim 1 further comprising at least one mirror locatable in a radiation beam path to permit location of the scanning light source out of the beam path.

5. The multi-leaf collimator according to claim 1 in which the scanning pattern illuminates a point that moves along the longitudinal edges of a plurality of leaves of the array in succession.

6. The multi-leaf collimator according to claim 1 in which the scanning light source comprises a laser.

7. The multi-leaf collimator according to claim 1 in which the reflective element is retro-reflective.

8. The multi-leaf collimator according to claim 1 in which the leaves are mounted in a frame, on which is mounted at least one reflective object.

9. An apparatus for location-detection of an object according to claim 1, adapted to repeat the scanning pattern once a scan of the region has been completed.

10. A Radiotherapeutic apparatus comprising a multi-leaf collimator according to claim 1.

* * * * *